(12) United States Patent
Ma et al.

(10) Patent No.: US 8,609,414 B2
(45) Date of Patent: Dec. 17, 2013

(54) ISOLATION AND GROWTH OF STEM CELLS FROM HEMANGIOMAS

(76) Inventors: Yupo Ma, Las Vegas, NV (US); Louis M. Fink, Las Vegas, NV (US); David C. Ward, Las Vegas, NV (US); Milton Waner, New York, NY (US)

( * ) Notice: Subject to any disclaimer, the term of this patent is extended or adjusted under 35 U.S.C. 154(b) by 0 days.

(21) Appl. No.: 13/167,493

(22) Filed: Jun. 23, 2011

(65) Prior Publication Data

US 2012/0117672 A1    May 10, 2012

Related U.S. Application Data

(63) Continuation of application No. 12/130,656, filed on May 30, 2008, now abandoned, which is a continuation-in-part of application No. 11/809,871, filed on Jun. 1, 2007, now abandoned.

(60) Provisional application No. 61/050,131, filed on May 2, 2008.

(51) Int. Cl.
*C12N 5/00*    (2006.01)
*C12N 5/02*    (2006.01)

(52) U.S. Cl.
USPC ............................ 435/378; 435/384; 435/383

(58) Field of Classification Search
None
See application file for complete search history.

(56) References Cited

PUBLICATIONS

Khan et al (Jour Clin Invest, 118:2592-2599, 2008).*
Yu et al, (Stem Cells, 1996, 24:1605-1612).*
Hermann (Cell Stem Cell, 2007, 1:313-323).*
Dontu (2003, Genes and Development, 17:1253-1270).*
Galli, Cancer Res, 2004,64:7011-7021.*

* cited by examiner

*Primary Examiner* — Valarie Bertoglio
(74) *Attorney, Agent, or Firm* — Blank Rome LLP

(57) ABSTRACT

The present invention describes stem cells and progenitor cells derived from hemangiomas, including testing of angiogenic inhibitors using these cells. The invention as described is useful in providing a process to culture and propagate hemangioma stem cells and generate xenograft models to develop treatments for infantile hemangiomas and other types of vascular lesions.

2 Claims, 8 Drawing Sheets

ISOLATION AND GROWTH OF STEM CELLS FROM HEMANGIOMAS

CROSS REFERENCE TO RELATED APPLICATION

This application is a continuation of U.S. application Ser. No. 12/130,656, filed May 30, 2008, now abandoned, which claims the benefit of and priority under 35 U.S.C. §120 as a continuation-in-part of U.S. application Ser. No. 11/809,871, filed Jun. 1, 2007 now abandoned, and claims benefit of and priority under 35 U.S.C. §119(e) to U.S. Provisional Application No. 61/050,131, filed May 2, 2008, the disclosures, each of are incorporated by reference in their entireties.

FIELD OF THE INVENTION

The present invention relates generally to stem cells, and more specifically to progenitor cells and stem cells isolated from human infantile hemangiomas, methods for culturing such cells, and methods of treating disorders associated with hemangiomas.

BACKGROUND INFORMATION

Infantile hemangiomas, the most common tumors of infancy, are vascular tumors characterized by rapid proliferation of endothelial cells during the first few months of postnatal life followed by slow spontaneous involution. Most disappear spontaneously (immature hemangiomas), while others persist and create cosmetic problems. Complications may follow overtreatment, posttraumatic ulceration, or localized tissue hypertrophy from a persistent angioma of the CNS, the face or an extremity.

While many hemangiomas eventually "involute," the result is not always cosmetically acceptable. Early intervention has been shown to reduce the need for corrective surgery after "involution" has occurred, or to, at least, minimize extensive corrective surgeries in the future. Psycho-social scarring which occurs when a child has been forced to live with a facial deformity until "involution" has been completed can be avoided by early, aggressive intervention, according to presently known treatment options.

Conventional treatment options for hemangiomas range from surgical excision (followed, in cases of facial or neck hemangiomas, with cosmetic surgery) to systemic corticosteroid treatments, laser, and use of alpha-interferon. Recently, cryosurgery and sclerotherapy, have been proposed additions to the available treatment regimens for hemangiomas.

Each conventional treatment option carries potential side effects. Clearly, surgery always presents risks, whether for infection, unexpected patient reaction to anesthesia, and/or unexpected aesthetic results.

While systemic corticosteroid treatment is suspected of certain side effects, regardless of age, steroid treatment carries decided risks if carried on beyond a child's first birthday. Furthermore, hemangiomas do not warrant nor benefit from steroids beyond the first birthday, in part, because proliferation of hemangiomas tends to end by that point anyway. In any event, if steroids are lowered too quickly or given intermittently, "rebound growth" is possible, if not likely. Some investigators have reported other side effects from steroid treatments. In one investigation, children (29 percent) became more irritable, depressed and/or napped less during treatment, although this resolved as treatment was tapered and discontinued. Other short-term side effects included gastric irritation, oral or perineal yeast infection, recurrent otitis media, hypertension, and myopathy.

As stated above, another treatment is sclerotherapy (i.e., injection of a chemical irritant into a vein to "harden" it). The disadvantages of sclerotheraphy include the pain of injection, swelling, and psychological strain associated therewith, as well as the danger of necrosis if the sclerosis technique is flawed.

While certain treatments for hemangiomas are considered typically effective, the psychological effects of hemangiomas alone warrant continued pursuit of more effective treatment regimens for hemangiomas, whether for use alone, or in concert with existing treatment options. Also, because most patients receiving treatments are infants or small children, patient tolerance for the treatment options becomes of more paramount importance.

SUMMARY OF THE INVENTION

The present invention is based on the seminal discovery that a stem cell population can be obtained from a hemangioma. Such cells are useful as a tool for developing treatments of infantile hemangiomas and other types of vascular lesions as well as for identifying agents that are anti-angiogenic.

In one embodiment, a stem cell or progenitor cell derived from hemangioma tissue is disclosed, where the stem cell or progenitor cell self renews in culture. The stem cell or progenitor typically forms a tumor sphere from a single cell in suspension.

In one aspect, the tumor sphere is enriched for cells which express CD133 or SALL4, or a combination thereof. In another aspect, the cells can be cultured in vitro in the absence of serum or serum replacement.

In a related aspect, the stem cell is capable of differentiating into endothelial-like tissue when the cell is contacted with vascular endothelial cell growth factor (VEGF).

In another embodiment, a method of screening agents that modulate cell proliferation is disclosed. In one aspect, the method includes contacting a progenitor cell or stem cell from hemangioma tissue with a test agent, comparing a characteristic property of the cells in the presence of the agent with the characteristic property in the absence of the test agent, and determining the effect of the test agent on the property. For example, a test agent modulates cell proliferation when a change in a property associated with the stem cell is affected (e.g., tumor sphere formation). In another aspect, a property includes, but is not limited to, growth characteristics; karyotype; immunohistochemical profile; gene expression profile; self-renewal capacity; and/or differentiation capacity.

In another aspect, the growth characteristics of a progenitor or stem cell are determined by contacting the progenitor or stem cell contained within a xenograft transplanted in a non-human animal. In a further aspect, the immunohistochemical profile is defined by one or more tissue specific markers, and includes, but is not limited to, GLUT-1, merosin, Fc-gamma-RII, Lewis Y antigens, β4-integrin, CD133, or SALL4, or a combination thereof.

In another aspect, the step of determining an effect of a test agent on a stem or progenitor cell includes generating global maps for SALL4 promoter binding in the presence and absence of the agent.

In one aspect, the method includes determining the effect of the test agent on a stem cell or progenitor cell in the presence and absence of an angiogenesis inhibitor, where the inhibitor includes VEGFR-1, NRP-1, angiopoietin 2, TSP-1, TSP-2, angiostatin, endostatin, vasostatin, calreticulin, platelet factor 4, IMP, CDAI, Meth-1, Meth-2, INF-α, INF-β, INF-γ, CXCL10, IL-4, IL-12, IL-18, prothrombin (kringle domain-2) antithrombin III fragment, prolactin, VEGI, SPARC, osteopontin, maspin, canstatin, proliferin-related protein, restin, bevacizumab, carboxyamidotriazol, TNP-470, CM101, suramin, thrombospondin, angiostatic steroids/heparin, cartilage-derived angiogenesis inhibitory factor, matrix metalloproteinase inhibitors, 2-methoxyestradiol, Tecogalan, $\alpha_v\beta_3$ inhibitors, or linomide.

In another embodiment, a non-human animal containing a xenograft transplant is disclosed, where the non-human animal contains an immortalized hemangioma cell-derived progenitor cell, stem cell, or differentiated cell from human infantile hemangioma tissue, and where the stem cell or progenitor cell self renews in culture, and which cell forms a tumor sphere from a single cell in suspension. In a related aspect, the differentiated cell is an endothelial-like cell. In a further related aspect, the non-human animal is murine, e.g., a mouse.

In one embodiment, a tumor sphere is disclosed which is derived from an hemangioma cell and includes a progenitor cell or stem cell from human infantile hemangioma tissue. In a related aspect, the tumor sphere comprises cells which express CD133 or SALL4, or a combination thereof.

In another embodiment, a method of producing stem cells from hemangiomas is disclosed including isolating cells from hemangioma tissue, culturing the isolated cells from the tissue in serum free media until tumor spheres are formed, isolating cells from the tumor spheres, and culturing the isolated cells from the tumor spheres in serum free media. The cells are typically characterized as a single cell type via expression of SALL4 or CD133, or a combination thereof.

In one embodiment, a method is provided for treating a hemangioma including administering an agent identified in the methods of screening herein. In a related aspect, the method includes co-administering one or more of the angiogenesis inhibitors including VEGFR-1, NRP-1; angiopoietin 2, TSP-1, TSP-2, angiostatin, endostatin, vasostatin, calreticulin, platelet factor 4, IMP, CDAI, Meth-1, Meth-2, INF-α, INF-β, INF-γ, CXCL10, IL-4, IL-12, IL-18, prothrombin (kringle domain-2) antithrombin III fragment, prolactin, VEGI, SPARC, osteopontin, maspin, canstatin, proliferin-related protein, restin, bevacizumab, carboxyamidotriazol, TNP-470, CM101, suramin, thrombospondin, angiostatic steroids/heparin, cartilage-derived angiogenesis inhibitory factor, matrix metalloproteinase inhibitors, 2-methoxyestradiol, Tecogalan, $\alpha_v\beta_3$ inhibitors, or linomide.

In another embodiment, a method of screening combinations of agents that modulate cell proliferation is disclosed including contacting hemangioma derived stem cells with one or more first agents that induce differentiation of a subpopulation of cells; allowing the subpopulation of cells to differentiate; contacting the differentiated cells with a second agent; and determining the affect of the second agent on the differentiated cells, where combining the first and second agents modulates proliferation of the differentiated cell.

DETAILED DESCRIPTION OF THE INVENTION

Figure 1:
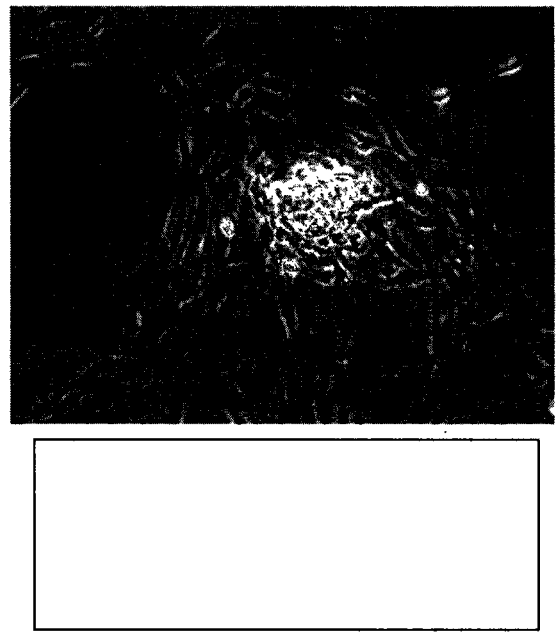
FIG. 1 is a photomicrograph showing the initial formation of a tumor sphere derived from primary culture. The tumor sphere is beginning to form with fibroblast cells derived from the tissue sample surrounding the forming sphere.

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a cell" includes one or more cells, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein "angioma," including grammatical variations thereof, means a localized vascular lesion of the skin and subcutaneous tissues, rarely of the CNS, that result from hyperplasia of the blood or lymph vessels. For example, angiomas include nevus flammeus hemangioma, infantile hemangioma, cavernous hemangioma, spider angioma, and lymphangiomas.

There are three major classifications of congenital hemangiomas: nevus flammeus (portwine stain); infantile hemangioma (capillary hemangioma or "strawberry mark"); and cavernous hemangioma.

Nevus flammeus hemangioma usually appears as a flat, pink, red, or purplish lesion present at birth. These lesions represent dilation of blood vessels commonly present in region of the back or nape of the neck. Nevus flammeus of the trigeminal area may be a component of the Sturge-Weber syndrome (leptomeningeal angiomatosis with intracranial calcification). A nevus flammeus usually will not fade, though splotchy small red macular lesions in the area above the nose and on the eyelids may disappear in a few months.

Cavernous hemangioma usually appears as a raised red or purplish lesion composed of large vascular spaces. The blood vessels and frequently the lymphatics are often immature, in which case the lesion may contain numerous arteriovenous shunts (i.e., a direct connection between an artery and vein) and vascular malformations. Cavernous hemangiomas rarely involute spontaneously. Partial involution may follow ulceration, trauma, or hemorrhage.

Infantile hemangioma usually appears as a raised bright red lesion consisting of proliferations of endothelial cells. It develops shortly after birth and tends to enlarge slowly during the first several months of life. About 75 to 95% usually involute spontaneously within 5 to 7 years; regression however is usually incomplete, and at times a brownish pigmentation and scarring or wrinkling of the skin remains.

Infantile hemangiomas arise from the over proliferation of endothelial cells and present themselves as vascular appearing tumors. These tumors are generally self involuting over time, but can present complications if excessively large. Further, these benign tumors arise shortly after birth with a proliferative phase lasting up to one year. Following the proliferative phase is a several year period of tumor regression. Usually this results in complete regression of the vasculature. In rare cases, these tumors can last well into middle age of adults. Surgical procedures to remove the vasculature are often quite complicated due to location and shear size of the tumor. However, removal of these disfiguring tumors is highly desirable for much of the population. The molecular nature of these tumors is unknown, yet may provide an opportunity to cure a currently incurable disease.

Routine histopathology varies according to the stage of the hemangioma. In early proliferation, hemangiomas are characterized by nonencapsulated masses and dense cords of mitotically active, plump endothelial cells in close association with pericytes. Few, small caliber lumina are present. Special stains reveal well-developed basement membranes around primitive vessels. Mast cells are present in varying numbers in all stages. As the hemangioma proliferates, the vascular lumina enlarge. An increase of apoptotic endothelial cells and a decrease in plump, mitotically active endothelial cells herald the involution phase. As involution progresses, the endothelial cells continue to mature and assume a flatter appearance. The vascular lumina continue to enlarge until few, mature ectatic vessels remain. Much of the proliferating endothelial cell mass is replaced with fibro-fatty tissue. Varying degrees of epidermal atrophy, scar tissue, and loss of elastic tissue can be seen in late involuting lesions.

While not being bound by theory, hemangiomas may fundamentally be a stem cell disease. In the classical model for tumors, phenotypically distinct cell populations all have equivalent self renewal and proliferative capacity, where tumor cell heterogeneity results from environmental factors as well as ongoing mutations within tumor cells that give rise to diverse populations of cells having similar tumorigenic potential. Alternatively, tumors may contain a limited subset of cells that share properties in common with stem cells in that they possess indefinite capacity for self renewal and are capable of differentiation into other cell types.

The present invention is based on the alternative model, where hemangiomas may be caused by either over-proliferation of a stem cell or progenitor cell population responsible for giving rise to the vasculature of hemangiomas, or, alternatively, a loss in regulation of differentiation of these cell populations. Following this model, the involution described following the first years of life corresponds to the depletion of these stem cell or progenitor cell populations. It is likely that this depletion is from the aging of the stem cell/progenitor cells resulting in apoptosis of these cells. Conversely, these cell populations may also undergo a terminal cell division resulting in the loss of self-renewal capabilities and leading to tumor regression.

Currently, there is no cell line or mouse model available to study infantile hemangiomas. These deficiencies render further understanding of the cellular biology and genetic events involved in infantile hemangiomas nearly impossible. In addition, testing the existing angiogenic inhibitors and screening new drugs for treatment of infantile hemangiomas has historically been a difficult task due to the lack of a cell line or mouse model. The ability to identify cell populations within hemangiomas, based on structural features, lineage markers, growth characteristics, expression profiles, and the like as described herein, allows the skill artisan to distinguish cell populations within such angiomas that possess indefinite self renewal capacity (i.e., stem cells) from cells which are depleted of this activity.

The present invention discloses the identification and isolation of a population of cells that possess indefinite self renewal capacity generated from tumor spheres derived from hemangioma tissue: i.e., hemangioma derived stem cells. In one embodiment, a composition comprising an enriched population of stem cells is disclosed, where the stem cells form tumor spheres in vitro or in vivo. As used herein "stem cell" means a relatively undifferentiated cell that retains the ability to divide to provide cells that can be specialized and take the place of cells that die or are lost. Further, "tumor sphere" means a globular cell cluster that may be formed in suspension that contains progenitor/stem cells, which cells retain self renewal capacity. Moreover, such tumor spheres include clonally derived non-adherent colonies of cells derived from a single tumor stem cell.

The cells described herein may be evaluated for tissue-specific markers such as GLUT-1, merosin, Fc-gamma-RII, and Lewis Y antigens. These markers may aid in differentiating infantile hemangiomas (positive staining for all) from other vascular neoplasms or malformations, such as the congenital hemangiomas (e.g., rapidly involuting congenital hemangioma, noninvoluting congenital hemangioma), kaposiform hemangioendothelioma, tufted angioma, or pyogenic granuloma, none of which stains positively for these antigens. These markers are coexpressed by infantile hemangiomas and placental microvessels. The present invention demonstrates that hemangioma tissues comprise a population of stem cells which express SALL4 and/or CD133. Accordingly, stem cells of the present invention may be further described by the determining the percentage of cells which express SALL4 and/or CD133.

SALL4 (and its isoforms SALL4A, SALL4B, and SALL4C), is a human homolog to Drosophila spalt and belongs to a group of $C_2H_2$ zinc finger transcription factors characterized by multiple finger domains distributed over the entire protein. CD133 is a cell surface protein expressed in hematopoietic stem cells, neuronal stem cells, glial stem cells, and endothelial progenitor cells. Expression of CD133 can serve as a marker for primitive cells.

In one aspect, the enriched population of hemangioma derived stem cells may be defined as comprising a population of SALL4 and/or CD133 positive cells that is greater than the concentration of SALL4 and/or CD133 positive cells in a non-concentrated hemangioma tissue preparation obtained from a subject with an angioma. As used herein "derived," including grammatical variations thereof, means to be obtained from a parent source. For example, stem cells of the present invention may be obtained from hemangioma tissue biopsied from a subject with an angioma. In one embodiment, the hemangioma derived stem cells may be obtained by isolating cells from primary hemangioma tissue or a primary hemangioma tumor sphere, culturing the cells in serum free media until tumor spheres are formed, isolating cells from the tumor spheres, and culturing the isolated cells in serum free media. In a related aspect, the hemangioma derived stem cells are immortal. As used herein "immortal," including grammatical variations thereof, means to change a cell population with a finite life span to one possessing a life span that may be maintained indefinitely under specific conditions.

In another aspect, the enriched preparations of the invention may be described as a function of the percentage of cells having self renewal capacity. As used herein "self renewal capacity" or "self renewal" means the ability of a cell to possess the property of cell division which results in one or both daughter cells (progeny) that have essentially the same ability to replicate and generate differentiated cell lineages as the progenitor cell. As used herein "progenitor cell" means a parental cell that gives rise to a distinct cell lineage by a series of cell divisions. Further, "differentiation capacity," as used herein, means the ability of cell to give rise to a distinct cell lineage.

The enriched preparation of the invention may further be described as a function of the percentage of SALL4 and/or CD133 positive cells that are capable of giving rise to a tumor sphere as compared to a non-enriched population. Further, the stem/progenitor cells of the present invention may be characterized by, for example, tumor cell formation, growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by Enzyme Linked ImmunoSorbent Assay (ELISA)), and/or other methods known in the art. Moreover, the stem/progenitor cells may be analyzed by limiting dilution assay, primary sphere formation assay, and/or cell proliferation assay.

Another key property of stem cells of the present invention is their ability to differentiate into mature cells. In one embodiment, hemangioma tumor sphere cells are capable of differentiating into mature cells, when such tumor cells are cultured in appropriate growth factors. Accordingly, the enriched population of the present invention may also be described as a function of the percentage of SALL4 and/or CD133 positive cells which differentiate into mature cells. For example, cells from hemangioma tumor spheres grown in VEGF differentiate into the endothelial-like tissue (see Example 1). As used herein "endothelial-like" means a cell which possesses morphology and/or express markers that are normally characteristic of endothelial cells. For example, morphologically, endothelial cells are flattened cells of mesoblastic origin. Further, endothelial cells express markers which include, but are not limited to, CD31, von Willebrand factor, vascular endothelial growth factor receptor 1, zonula occludens 1, and occludin.

The culture medium to support the growth and proliferation of the cells of the present invention may be a chemically defined serum-free medium that is supplemented with a source of mitogens and survival factors to allow the growth of stem cells in culture.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C. Similarly, cells may be cultured in levels of $O_2$ that are comparatively reduced relative to $O_2$ concentrations in air, such that the $O_2$ concentration is comparable to physiological levels (1-6%), rather than 20% $O_2$ in air.

For example, primary cells may be cultured in KNOCKOUT™ Dulbecco's Modified Eagle's Medium (DMEM), 10% KNOCKOUT™ Serum, 1× non-essential amino acids (NEAA), and 20 µg/ml basic-fibroblast growth factor (bFGF). Following growth of a primary culture for approximately 1 to 2 day, 2 to 3 days, 3 days to 1 week, tumor spheres will spontaneously form from the homogenous mixture of primary culture. Spheres may be collected using collagenase digestion, washed, and plated at an appropriate density (e.g., 200 cells per milliliter) with DMEM-F12 nutrient mix, 20 µg/ml bFGF and NEAA on low-attachment plates. The tumor spheres form and propagate using collagenase digestion, which digests the spheres to single cells. These single cells may then be used to form additional tumor spheres in vitro or grafts in vivo. The stem cells of the present invention and stem cell progeny may also be cryopreserved until they are needed by any method known in the art. The cells can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15%, preferably 8-10%. Cells are frozen gradually to a temperature of −10° C. to −150° C., preferably −20° C. to −100° C., and more preferably −150° C. Further, the stem cells of the present invention may be used to produce immortalized cell lines.

In one embodiment, due to the vascular origin of the benign tumor, testing angiogenic inhibitors in vitro and in vivo may be used to improve various treatment modalities. Additionally, screening methods for identifying new drugs that target key mechanisms in hemangioma propagation or specific genes with vital roles in infantile hemangioma proliferation are also disclosed.

In one embodiment, a method of screening test agents that modulate cell proliferation is disclosed including contacting a stem cell from hemangioma tissue with an test agent, comparing a characteristic property associated with the cells in the presence of the agent with the characteristic property in the absence of the test agent, and determining the affect of the test agent on the property, where a test agent modulates (increases or decreases) cell proliferation when a change in a property associated with the stem cell is affected. In one aspect, the property includes growth characteristics; tumor sphere formation; karyotype; immunohistochemical profile; gene expression profile; self-renewal capacity; and differentiation capacity. In one aspect, one or more agents may induce apoptosis of the stem cell.

In another aspect, such agents may be beneficial in other vascular legions arising from endothelial cells or similar stem/progenitor cells. Further, the methods of the present invention provide an avenue to culture and propagate hemangioma stem cells, and generate grafts in non-human animals.

In one aspect, tumor spheres of the present invention may be used as a xenograft. As used herein the term xenograft refers to a tissue or organ, for example a tumor or a nondispersed piece of a tumor, from a donor of one species, placed into a recipient of another species.

Xenografts allow for in vivo proliferation of the tumor sphere derived cells. The in vivo proliferation of the cells of the present invention may be accomplished by injection of the cells into non-human animals, preferably mammals, including murine species.

In one embodiment, a non-human animal containing a xenograft transplant is disclosed, where the non-human animal contains a differentiated cell from human infantile hemangioma tissue, and where the stem cell or progenitor cell self renews in culture. In a related aspect, the differentiated cell is an endothelial-like cell. As xenografts may be rejected by an intact immune system of the recipient, in some embodiments the recipient is chosen or manipulated to have an incompetent immune system. In one embodiment, the recipient is a SCID mouse, Beige/SCID mouse, NOD/SCID mice. The mouse is injected with varying numbers of cells and observed for tumor formation. The injection method may be any method known in the art, following the enrichment of the injected population of cells.

Thus, the present invention provides an approach for the treatment of infantile hemangiomas through analysis of an in vitro and/or in vivo system. These systems allow for the development of novel treatments for infantile hemangiomas and other types of vascular lesions.

In one embodiment, a method of treating hemangiomas is disclosed, including administering an agent identified by the screening method above. In a related aspect, the method may further include co-administration of one or more angiogenesis inhibitors such as VEGFR-1, NRP-1; angiopoietin 2, TSP-1, TSP-2, angiostatin, endostatin, vasostatin, calreticulin, platelet factor 4, IMP, CDAI, Meth-1, Meth-2, INF-α, INF-β, INF-γ, CXCL10, IL-4, IL-12, IL-18, prothrombin (kringle domain-2) antithrombin III fragment, prolactin, VEGI, SPARC, osteopontin, maspin, canstatin, proliferin-related protein, restin, bevacizumab, carboxyamidotriazol, TNP-470, CM101, suramin, thrombospondin, angiostatic steroids/heparin, cartilage-derived angiogenesis inhibitory factor, matrix metalloproteinase inhibitors, 2-methoxyestradiol, Tecogalan, $\alpha_v\beta_3$ inhibitors, and linomide.

The observation that only a sub-population of hemangioma cells are stem cells, which cells maintain the ability to give rise to cells by self renewal, suggests that involution occurs when these cells lose this capacity. By screening agents which modulate the self renewal/differentiation capacity of the cells of the present invention, identification of therapeutic modalities which only affect this sub-population may be identified. For example, SALL4 expression maintains self-renewal properties in embryonic stems cells (ESC), including that when SALL4 expression is inhibited, self-renewal capacity may be modulated in these cells. In one embodiment, a method of screening agents is disclosed including contacting the cells of the present invention with an agent which reduces the expression levels of SALL4. Agents include, but are not limited to, known inhibitors of SALL4 expression such as methylation inhibitors, including 5' azacytidine, 5' aza-2-deoxycytidine, 1-B-D-arabinofuranosyl-5-azacytosine, or dihydroxy-5-azacytidine, and proteosome inhibitors including MG132, PSI, lactacystin, expoxomicin, or bortezomib.

The present invention also discloses that VEGF-induced differentiated cells derived from hemangioma tumor spheres are CD133 negative (Example 1), suggesting that differentiation of the hemangioma derived stem cells results in loss of self renewal capacity. As such, hemangiomas may be treated by "differential sensitization," where the subpopulation of CD133 positive cells in the tumor sphere are induced to differentiate by contacting such cells with a first agent, including but not limited to a growth factor, and subsequently contacting the differentiated cells with a second agent that modulates a property associated with the differentiated cell. In one embodiment, agents for use in differential sensitization may be screened by contacting a hemangioma tumor sphere with one or more agents that induce differentiation of CD133 positive cells, subsequently allowing the CD133 positive cells to differentiate, contacting the cells with a second agent, and determining the affect of the second agent on the differentiated cell, where the combination of the first and second agent modulates proliferation of the differentiated cell (e.g., induces apoptosis). In one aspect, differentiation may be determined by detecting the presence or absence of one or more cell-type differentiation markers. In another aspect, the first agent includes, but is not limited to, retinoic acid, BMP, VEGF, GATA factors, EGF, FGF-2, PDGF, HGF, laminin, nicotinamide, GM-CSF, IL-3, collagen IV, dexamethasone, TGF-β, fibronectin, erythropoietin, thrombopoietin, G-CSF, TNF-α, and insulin. In a related aspect, the second agent includes, but is not limited to, small molecules, nucleic acids, proteins, polypeptides, peptides, and peptidomimetics. In one aspect, the second agent is an angiogenesis inhibitor, and includes, but is not limited to, VEGFR-1, NRP-1; angiopoietin 2, TSP-1, TSP-2, angiostatin, endostatin, vasostatin, calreticulin, platelet factor 4, IMP, CDAI, Meth-1, Meth-2, INF-α, INF-β, INF-γ, CXCL10, IL-4, IL-12, IL-18, prothrombin (kringle domain-2) antithrombin III fragment, prolactin, VEGI, SPARC, osteopontin, maspin, canstatin, proliferin-related protein, restin, bevacizumab, carboxyamidotriazol, TNP-470, CM101, suramin, thrombospondin, angiostatic steroids/heparin, cartilage-derived angiogenesis inhibitory factor, matrix metalloproteinase inhibitors, 2-methoxyestradiol, Tecogalan, $\alpha_v\beta_3$ inhibitors, and linomide.

Combination therapy according to the present invention may be performed alone or in conjunction with another therapy and may be provided at home, the doctor's office, a clinic, a hospital's outpatient department, or a hospital. The duration of the combination therapy depends on the type of vascular disorder being treated, the age and condition of the patient, the stage and type of the patient's disease, and how the patient responds to the treatment.

The compositions comprising agents of the present invention may be administered orally, topically, parenterally, by inhalation or spray or rectally in dosage unit formulations containing conventional non-toxic pharmaceutically acceptable carriers, adjuvants and vehicles.

The term "parenteral" as used herein includes percutaneous, subcutaneous, peritumoral, intravascular (e.g., intravenous), intramuscular, or intrathecal injection or infusion techniques and the like. In addition, there is provided a pharmaceutical formulation comprising an agent of the present invention and a pharmaceutically acceptable carrier. Such combinations may be present in association with one or more non-toxic pharmaceutically acceptable carriers and/or diluents and/or adjuvants, and if desired other active ingredients. The pharmaceutical compositions may be in a form suitable for oral use, for example, as tablets, troches, lozenges, aqueous or oily suspensions, dispersible powders or granules, emulsion, hard or soft capsules, or syrups or elixirs.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The combinations containing agents of the present invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

For disorders of external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream may be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

It will be understood that the specific dose level for any particular subject will depend upon a variety of factors including the activity of the specific compound employed, the age, body weight, general health, sex, diet, time of administration, route of administration, and rate of excretion, drug combination and the severity of the particular disease undergoing therapy.

In the undifferentiated state, the stem cells of the present invention divide and are therefore excellent targets for genetic modification. The term "genetic modification" as used herein refers to the stable or transient alteration of the genotype of a precursor cell by intentional introduction of exogenous DNA. DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like. General methods for the genetic modification of eukaryotic cells are known in the art. See, Sambrook et al., Molecular Cloning: A Laboratory Manual (Cold Spring Harbor Press, Cold Spring Harbor, N.Y., 1989); Current Protocols in Molecular Biology, Ausubel et al., eds., (Wiley Interscience, New York, 1993)).

Many methods for introducing vectors into cells or tissues are available and equally suitable for use with stem cells of the present invention in vivo, in vitro, and ex vivo. Vectors may be introduced into stem cells taken from the patient and clonally propagated.

"Transformation," or "genetically modified" as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment, and the like. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

Genetic modification of a cell may be accomplished using one or more techniques well known in the gene therapy field. Mulligan R C, Human Gene Therapy 5: 543-563 (1993). Viral transduction methods may comprise the use of a recombinant DNA or an RNA virus comprising a nucleic acid sequence that drives or inhibits expression of a protein to infect a target cell. A suitable DNA virus for use in the present invention includes but is not limited to an adenovirus (Ad), adeno-associated virus (AAV), herpes virus, vaccinia virus or a polio virus. A suitable RNA virus for use in the present invention includes, but is not limited to, a retrovirus or Sindbis virus. Several such DNA and RNA viruses exist that may be suitable for use in the present invention.

Adenoviral vectors have proven especially useful for gene transfer into eukaryotic cells (Graham F L & Prevec L, In Vaccines: New Approaches to Immunological Problems, Ellis R V ed., 363-390 (Butterworth-Heinemann, Boston, 1992).

"Non-viral" delivery include DNA-ligand complexes, adenovirus-ligand-DNA complexes, direct injection of DNA, $CaPO_4$ precipitation, gene gun techniques, electroporation, and lipofection. Mulligan R C, Science 260: 926-932 (1993). Any of these methods are widely available to one skilled in the art and would be suitable for use in the present invention. Other suitable methods are available to one skilled in the art, and it is to be understood that the present invention may be accomplished using any of the available methods of transfection. Lipofection may be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule. Delivery by transfection, by liposome injections, or by polycationic amino polymers may be achieved using methods which are well known in the art (see, e.g., Goldman, C. K. et al. Nature Biotechnology 15:462-466 (1997)).

Genetically modified stem cells of the present invention may be subjected to tissue culture protocols known in the art (see, U.S. Pat. Nos. 5,750,376 and 5,851,832, Spector et al., Cells: A Laboratory Manual (Cold Spring Harbor Press, Cold Spring Harbor, N.Y., 1998)). The stem cells may be genetically modified in culture to promote differentiation, cell death, or immunogenicity. For example, stem cells can be modified to enhance expression of products that direct an immune response against the patient's hemangioma. Alternatively, the stem cells may be subjected to various proliferation protocols in vitro prior to genetic modification. The protocol used depends upon the type of genetically modified stem cell desired.

DNA or RNA may be isolated from the stem cells of the present invention according to any of a number of methods well known to those of skill in the art. For example, methods of purification of nucleic acids are described in Tijssen, Laboratory Techniques in Biochemistry and Molecular Biology Hybridization With Nucleic Acid Probes, Part I. Theory and Nucleic Acid Preparation (Elsevier, New York N.Y., 1993). "Sample" is used in its broadest sense. A sample containing polynucleotides or polypeptides can be a bodily fluid; an extract from a cell, chromosome, organelle, or membrane isolated from a cell; genomic DNA, RNA, or cDNA in solution or bound to a substrate; a cell; a tissue; a tissue print; and the like.

Total RNA may be isolated using the TRIZOL reagent (Life Technologies, Gaithersburg Md., USA), and mRNA is isolated using oligo d(T) column chromatography or glass beads. Alternatively, when target polynucleotides are derived from an mRNA, the target polynucleotides may be a cDNA reverse transcribed from an mRNA, an RNA transcribed from that cDNA, a DNA amplified from that cDNA, an RNA transcribed from the amplified DNA, and the like. When the target polynucleotide is derived from DNA, the target polynucleotide may be DNA amplified from DNA or RNA reverse transcribed from DNA.

Several technologies produce pools of restriction fragments of limited complexity for electrophoretic analysis, such as methods combining double restriction enzyme digestion with phasing primers (see, e.g., European patent application EP 0 534 858 A1), or methods selecting restriction fragments with sites closest to a defined mRNA end (see, e.g., Prashar et al., Proc. Natl. Acad. Sci. USA 93: 659-663 (1996)). Other methods statistically sample cDNA pools, such as by sequencing sufficient bases (in each of multiple cDNAs to identify each cDNA, or by sequencing short tags which are generated at known positions relative to a defined mRNA end (see, e.g., Velculescu, Science 270: 484-487 (1995)).

Methods of modifying RNA abundances and activities currently fall within three classes, ribozymes, antisense species (PCT patent application WO 88/09810), and RNA aptamers (Good et al., Gene Therapy 4: 45-54 (1997)). Ribozymes are RNAs which are capable of catalyzing RNA cleavage reactions. (PCT patent application WO 90/11364). Ribozyme methods involve exposing a cell to, inducing expression in a cell, etc. of such small RNA ribozyme molecules. (Grassi & Marini, Annals of Medicine 28: 499-510 (1996); Gibson, Cancer and Metastasis Reviews 15: 287-299 (1996)).

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand. Such antisense molecules include interfering RNA (i.e., RNAi).

The term "RNAi" refers generally to a process in which a double-stranded RNA molecule changes the expression of a nucleic acid sequence with which the double-stranded or short hairpin RNA molecule shares substantial or total homology. While not being bound by theory, the mechanism of action may include, but is not limited to, direct or indirect down regulation of the expression of the SALL4 gene, decrease in SALL4 mRNA, and/or a decrease in SALL4 activity. The term "RNAi," including "short inhibitory RNA (siRNA)," refer to RNA sequences that elicit RNA interference, and which is transcribed from a vector. The terms "short hairpin RNA" or "shRNA" refer to an RNA structure having a duplex region and a loop region. This term should also be understood to specifically include RNA molecules with stem-loop or panhandle secondary structures. In some embodiments of the present invention, RNAis are expressed initially as shRNAs.

RNAi is generally optimised by identical sequences between the target and the RNAi. The RNA interference phenomenon can be observed with less than 100% homology, but the complementary regions must be sufficiently homologous to each other to form the specific double stranded regions. The precise structural rules to achieve a double-stranded region effective to result in RNA interference have not been fully identified, but approximately 70% identity is generally sufficient. Accordingly, in some embodiments of the invention, the homology between the RNAi and SALL4 is at least 70% nucleotide sequence identity, and may be at least 75% nucleotide sequence identity. Homology includes, but is not limited to, at least 80% nucleotide sequence identity, and is at least 85% or even 90% nucleotide sequence identity. In one embodiment, sequence homology between the target sequence and the sense strand of the RNAi is at least 90%, 91%, 92%, 93%, 94%, 95%, 96%, 97%, 98%, 99% or 100% nucleotide sequence identity.

Another consideration is that base-pairing in RNA is subtly different from DNA in that G will pair with U, although not as strongly as it does with C, in RNA duplexes. Moreover, for RNAi efficacy, it is more important that the antisense strand be homologous to the target sequence. In some circumstances, it is known that 17 out of 21 nucleotides is sufficient to initiate RNAi, but in other circumstances, identity of 19 or 20 nucleotides out of 21 is required. While not being bound by theory, at a general level, greater homology is required in the central part of a double stranded region than at its ends. Some predetermined degree of lack of perfect homology may be designed into a particular construct so as to reduce its RNAi activity which would result in a partial silencing or repression of the target gene's product, in circumstances in which only a degree of silencing was sought. In such a case, only one or two bases of the antisense sequence may be changed. On the other hand, the sense strand is more tolerant of mutations. While not being bound by theory, this may be due to the antisense strand being the one that is catalytically active. Thus, less identity between the sense strand and the transcript of a region of a target gene will not necessarily reduce RNAi activity, particularly where the antisense strand perfectly hybridizes with that transcript. Mutations in the sense strand (such that it is not identical to the transcript of the region of the target gene) may be useful to assist sequencing of hairpin constructs and potentially for other purposes, such as modulating dicer processing of a hairpin transcript or other aspects of the RNAi pathway.

The terms "hybridizing" and "annealing" including grammatical equivalents thereof, are used interchangeably in this specification with respect to nucleotide sequences and refer to nucleotide sequences that are capable of forming Watson-Crick base pairs due to their complementarity. The person skilled in the art would understand that non-Watson-Crick base-pairing is also possible, especially in the context of RNA sequences. For example a so-called "wobble pair" can form between guanosine and uracil residues in RNA.

The RNA expression products lead to the generation of a double-stranded RNA (dsRNA) complex for inducing RNA interference and thus down-regulating or decreasing expression of a mammalian gene. "dsRNA" refers to a ribonucleic acid complex comprising two Watson-Crick base-paired complementary RNA strands. The dsRNA complex comprises a first nucleotide sequence that hybridizes under stringent conditions, including a wash step of 0.2×SSC at 65° C., to a nucleotide sequence of at least one mammalian gene and a second nucleotide sequence which is complementary to the first nucleotide sequence. The first nucleotide sequence might be linked to the second nucleotide sequence by a third nucleotide sequence (e.g., an RNA loop) so that the first nucleotide sequence and the second nucleotide sequence are part of the same RNA molecule; alternatively, the first nucleotide sequence might be part of one RNA molecule and the second nucleotide sequence might be part of another RNA molecule. Thus, a dsRNA complex may be formed by intramolecular hybridization or annealing or the ds RNA complex is formed by intermolecular hybridization or annealing.

Oligonucleotides may be synthesized by standard methods known in the art, e.g. by use of an automated DNA synthesizer (such as are commercially available from Biosearch, Applied Biosystems, etc.).

"Amplification," as used herein, relates to the production of additional copies of a nucleic acid sequence. Amplification is generally carried out using polymerase chain reaction (PCR) technologies well known in the art. See, e.g., Dieffenbach C W & Dveksler G S, PCR Primer, a Laboratory Manual 1-5 (Cold Spring Harbor Press, Plainview, N.Y., 1995). Amplification can be polymerase chain reaction (PCR), ligase chain reaction (LCR), nucleic acid sequence-based amplification (NASBA), or T7 based RNA amplification.

"Polypeptide" refers to an amino acid, amino acid sequence, oligopeptide, peptide, or protein or portions thereof whether naturally occurring or synthetic.

Methods for direct measurement of protein activity are well known to those of skill in the art. Such methods include, e.g., methods which depend on having an antibody ligand for the protein, such as Western blotting, see, e.g., Burnette, A. Anal. Biochem. 112: 195-203 (1981). Such methods also include enzymatic activity assays, which are available for most well-studied protein drug targets. Detection of proteins can be accomplished by antibodies.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

Proteins isolated from an enriched population of stem cells can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al, Gel Electrophoresis of Proteins: A Practical Approach (IRL Press, New York 1990); Lander, Science 274:536-539 (1996). The resulting electrophoretograms can be analyzed by numerous techniques, including mass spectrometric techniques, western blotting and immunoblot analysis using polyclonal and monoclonal antibodies, and internal and N-terminal microsequencing. Using these techniques, it is possible to identify a substantial fraction of all the proteins produced under given physiological conditions, including in cells (e.g., in hemangioma derived stem cells) exposed to a drug, or in cells modified by, e.g., deletion or over-expression of a specific gene.

The purified stem cells of the present invention may be used to make arrays or cDNA libraries using methods known in the art (see, Sambrook et al., Molecular Cloning: A Laboratory Manual (Cold Spring Harbor Press, Cold Spring Harbor, N.Y., 1989); Current Protocols in Molecular Biology, Ausubel et al., eds., (Wiley Interscience, New York, 1993)) to identify potential novel drug targets.

Molecular biology comprises a wide variety of techniques for the analysis of nucleic acids and proteins, many of which form the basis of clinical diagnostic assays. These techniques include nucleic acid hybridization analysis, restriction enzyme analysis, genetic sequence analysis, and separation and purification of nucleic acids and proteins (Sambrook et al., Molecular Cloning: A Laboratory Manual, Second Ed. (Cold Spring Harbor Laboratory Press, Cold Spring Harbor, N.Y., 1989). Many molecular biology techniques involve carrying out numerous operations on a large number of samples. For guidance to genomics and other molecular biological methods useful in the invention, see Birren et al., Genome Analysis: A Laboratory Manual Series, Volume 1, Analyzing DNA (Cold Spring Harbor Press, Cold Spring Harbor, N.Y., 1997); Birren et al., Genome Analysis: A Laboratory Manual Series, Volume 2, Detecting Genes (Cold Spring Harbor Press, Cold Spring Harbor, N.Y., 1998); Birren et al., Genome Analysis: A Laboratory Manual Series, Volume 4, Mapping Genomes (Cold Spring Harbor Press, Cold Spring Harbor, N.Y., 1999).

Nucleic acid hybridization analysis generally involves the detection of a very small numbers of specific target nucleic acids (DNA or RNA) with probes among a large amount of non-target nucleic acids. Multiple sample nucleic acid hybridization analysis has been conducted on a variety of filter and solid support formats. The "dot blot" hybridization, involves the non-covalent attachment of target DNAs to a filter, which are subsequently hybridized with a labeled probes. The "dot blot" hybridization has been further developed for multiple analysis (European Patent application EP 0 228 075) and for the detection of overlapping clones and the construction of genomic maps (U.S. Pat. No. 5,219,726). Another format, the so-called "sandwich" hybridization, involves attaching oligonucleotide probes covalently to a solid support and using them to capture and detect multiple nucleic acid targets (U.S. Pat. No. 4,751,177; PCT International patent application WO 90/01564). Multiplex versions of these formats are called "reverse dot blots."

Methods are known in the art for amplifying signal using sensitive reporter groups (enzyme, fluorophores, radioisotopes, etc.) and associated detection systems (fluorometers, luminometers, photon counters, scintillation counters, etc.). These methods can be combined with amplification methods, such as the polymerase chain reaction (PCR) for the amplification of target nucleic acid sequences. See, Innis et al., PCR Protocols: A Guide to Methods and Applications, (Academic Press, 1990).

Analysis of the nucleic acids of the hemangioma derived stem cells of the present invention may be carried out using multiple sample nucleic acid hybridization methods on micro-formatted multiplex or matrix devices (e.g., DNA chips or microarrays) (see, Barinaga, Science 253: 1489 (1991); Bains, Bio/Technology 10: 757-758 (1992)). Guidance for the use of microarrays is provided by Wang, E et al, Nature Biotechnology 18; 457-459 (2000); Diehn M et al., Nature Genetics 25: 58-62 (2000).

Microarrays are known in the art and consist of a surface to which probes that correspond in sequence to gene products (e.g., cDNAs, oligonucleotides, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome.

The polynucleotides, polypeptides, or analogues are attached to a solid support or substrate, which may be made from glass, plastic (e.g., polypropylene, nylon), polyacrylamide, nitrocellulose, or other materials. "Substrate" refers to any suitable rigid or semi-rigid support to which polynucleotides or polypeptides are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores. The polynucleotides can be immobilized on a substrate by any method known in the art. Preferably, the substrates are optically transparent.

A variety of methods are currently available for making arrays of biological macromolecules, such as arrays of nucleic acid molecules or proteins. One method for making ordered arrays of DNA on a porous membrane is a "dot blot" or "slot-blot" method. A more efficient technique employed for making ordered arrays of fragments uses an array of pins dipped into the wells, e.g., the 96 wells of a microtiter plate, for transferring an array of samples to a substrate, such as a porous membrane. An alternate method of creating ordered arrays of nucleic acid sequences is described by U.S. Pat. No. 5,143,854 (to Pirrung), and also by Fodor et al., Science 251:767-773 (1991). The method involves synthesizing different nucleic acid sequences at different discrete regions of a support. Khrapko et al., DNA Sequence 1:375-388 (1991) describes a method of making an oligonucleotide matrix by spotting DNA onto a thin layer of polyacrylamide, manually with a micropipette. U.S. Pat. No. 5,807,522 (to Brown et al.) describes methods for fabricating microarrays of biological samples by dispensing a known volume of a reagent at each selected array position, by tapping a capillary dispenser on the support under conditions effective to draw a defined volume of liquid onto the support.

Spotters can use pin, ink-jet, and other technologies to deposit samples onto the support material. Several of the more common methods utilize metal pins, which can be either solid or split. When the pins are dipped into wells that contain the compounds of interest, each picks up a small amount of the material. The pin is then brought into contact with the solid support and a nanoliter volume is dispensed at the desired location. In split pins (otherwise known as quills) a slot cut into the head of the pin functions as a reservoir for the compound being spotted. Quill pins are most often used with glass slides, while solid pins are typically used for spotting membranes. Amersham Pharmacia Biotech, GeneMachines, and other companies offer spotting robots.

Ink jet technology provides another method of spotting microarrays. Adapted from the printer industry and redesigned for use in biotechnological applications, this uses piezoelectric crystal oscillators and an electrode guidance system to deposit the compound in a precise location on the slide or membrane. Companies such as Cartesian Technologies and ProtoGene Laboratories use this technology.

A method for attaching the nucleic acids to a surface is by printing on glass plates, as is described generally by PCT publication WO 95/35505; DeRisi et al., Nature Genetics 14:457-460 (1996); Shalon et al., Genome Res. 6:639-645 (1996); and Schena et al., Proc. Natl. Acad. Sci. USA 93: 10614-10619 (1995). Another method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., Science 251: 767-773 (1991); Pease et al., Proc. Natl. Acad. Sci. USA 91:5022-5026 (1994); Lockhart et al., Nature Biotech 14:1675 (1996); U.S. Pat. Nos. 5,578,832; 5,556,752; and 5,510,270).

U.S. Pat. No. 6,110,426 (to Shalon et al.) a method and apparatus for fabricating microarrays of biological samples for large scale screening assays, such as arrays of DNA samples to be used in DNA hybridization assays for genetic research and diagnostic applications. U.S. Pat. No. 6,221,674 (to Sluka et al.) discloses a process is described for applying spatially defined reagent areas to a solid phase which is characterized in that a liquid containing an adsorptive binding reagent is contacted with spatially defined areas of a solid phase which comprises an essentially continuous metal or metal oxide surface for an adequate time period to enable the formation of adsorptive bonds between the binding reagent and the solid phase. A process is described in PCT application WO 92/10092 which can be used to generate a plurality of different structures on a glass support by means of photoreactive compounds and irradiation using masks. A process is described in U.S. Pat. No. 4,877,745 in which differently functionalized spots can be applied to plastic supports by means of ink-jet.

Among the vendors of microarrays and microarray technology useage are Affymetrix, Inc. (USA), NimbleGen Systems, Inc. (Madison, Wis., USA), and Incyte Genomics (USA) (producing microarrays for core facilities in large industrial and academic departments); Agilent Technologies (USA) and Graffinity Pharmaceutical Design, GmbH (Germany) (which provide specific services such as printing and fingerprinting arrays designed and used by individual researchers); and CLONTECH Laboratories (Becton Dickinson Bioscience) and BioRobotics, Ltd. (Great Britain) (which provide the basic tools necessary for individual researchers to carry out the entire process of producing microarrays, including printing). See, Gwynne P & Heebner G, "DNA Chips and Microarrays" Science (2001).

In contrast to plastic surfaces, metal and metal oxide surfaces have the advantage that they can be coated with an exactly defined matrix layer by self-assembly techniques. A self-assembled monolayer (SAM) is formed for example when organic alkylthiols are adsorbed onto a gold surface, the spontaneous organisation of such a densely packed monolayer being based on strong specific interactions between the support material and the adsorbent. Nuzzo et al., J. Am. Chem. Soc. 105: 4481 (1983). In this manner it is possible to apply an exactly defined monolayer of a binding matrix to the surface of metals such as, e.g., gold or silver. Furthermore the specific binding capability of self-assembled solid phases can be further optimized by dilution of the specific solid phase reactants as described in EP-A-0 515 615.

The coating of metal surfaces with microstructures based on self-assembled monolayers is also known and can be used to attach components isolated from solid tumor stem cells. Whitesides et al., Langmuir 10 (1994) 1498-1511 describe a process in which reagents are stamped onto a noble metal surface by means of a special microstructured silicone stamp. This enables microstructured monolayers to be generated with zones that are spatially separated from one another. Microstructures of self-assembled monolayers on noble metal surfaces can be formed by irradiation through masks of substrates whose whole area is covered with thiols and subsequent washing. Hemminger et al., Langmuir 10: 626-628 (1994). Spatially separate zones are also formed in this process which are all identically functionalized. A further possibility of producing reagent spots is firstly to apply gold spots to a support that are already spatially separated from one another which are then subsequently coated with reagents.

The binding of analytes to a functionalized solid phase matrix according to the invention can for example be detected by confocal scanner fluorescence microscopy or by plasmon resonance spectroscopy. Ruthenhausler B et al., Nature, 332: 615-617 (1988).

U.S. Pat. No. 6,228,659 describes an apparatus for producing a plurality of arrays of reagent regions is disclosed. A dispensing assembly in the apparatus has a plurality of heads which are spaced for depositing reagents at selected positions in different array areas in a substrate.

Transcript arrays may be employed for analyzing the transcriptional state in a cell, and especially for measuring the transcriptional states of cells exposed to graded levels of a therapy of interest such as graded levels of a drug of interest or to graded levels of a disease state of interest. In one embodiment, transcript arrays are produced by hybridizing detectably labeled polynucleotides representing the mRNA transcripts present in a cell (e.g., fluorescently labeled cDNA synthesized from total cell mRNA) to a microarray. In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. The label for the probe may be selected from the group consisting of biotin, fluorescent, radioactive, and enzymatic labels. When fluorescently-labeled probes are used, many suitable fluorophores are known, including fluorescein, lissamine, phycoerytluin, rhodamine (Perkin Elmer Cetus), Cy2, Cy3, Cy3.5, Cy5, Cy5.5, Cy7, FluorX (Amersham) and others (see, e.g. Kricka, Nonisotopic DNA Probe Techniques (Academic Press San Diego, Calif., 1992). It will be appreciated that pairs of fluorophores are chosen that have distinct emission spectra so that they can be easily distinguished. In another embodiment, a label other than a fluorescent label is used. For example, a radioactive label, or a pair of radioactive labels with distinct emission spectra, may be used (see Zhao et al., Gene 156:207 (1995); Pietu et al., Genome Res. 6:492 (1996); see also, EXAMPLE 21). For example, $^{32}P$ may be used.

These methods of attaching transcripts usually attach specific polynucleotide sequences to very small specific areas of a solid support, such as micro-wells of a DNA chip. These hybridization formats are micro-scale versions of the conventional "reverse dot blot" and "sandwich" hybridization systems. The micro-formatted hybridization can be used to carry out "sequencing by hybridization" (see, Barinaga, Science 253: 1489 (1991); Bains, Bio/Technology 10: 757-758 (1992). Sequencing by hybridization makes use of all possible n-nucleotide oligomers (n-mers) to identify n-mers in an unknown DNA sample, which are subsequently aligned by algorithm analysis to produce the DNA sequence (see, U.S. Pat. No. 5,202,231; see also, United Kingdom patent application GB 8810400 (1988); Southern et al., Genomics 13: 1008 (1992); Fodor et al., Nature 364: 555-556 (1993); Fodor et al., Science 251: 767-773 (1991); U.S. Pat. No. 5,143,854.

Probes can be synthesized, in whole or in part, on the surface of a substrate using a chemical coupling procedure and a piezoelectric printing apparatus, such as that described in PCT publication WO 95/251116 (Baldeschweiler et al.). Alternatively, the probe can be synthesized on a substrate surface using a self-addressable electronic device that controls when reagents are added (U.S. Pat. No. 5,605,662).

Furthermore, the probes do not have to be directly bound to the substrate, but rather can be bound to the substrate through a linker group. The linker groups are typically about 6 to 50 atoms long to provide exposure to the attached polynucleotide probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the polynucleotide probe.

Devices and computer systems for forming and using arrays of materials on a chip or substrate are known. For example, PCT International patent applications WO 92/10588 and WO 95/11995, both incorporated herein by reference, describe techniques for sequencing or sequence checking nucleic acids and other materials. Arrays for performing these operations can be formed in arrays according to the methods of, for example, the pioneering techniques disclosed in U.S. Pat. Nos. 5,445,934, 5,384,261 and 5,571,639. Improved methods of forming high-density arrays of peptides, polynucleotides, and other polymer sequences in a short period of time have been devised using combinatorial solid phase synthesis. Very Large Scale Immobilized Polymer Synthesis (VLSIPS) technology has greatly advanced combinatorial solid phase polymer synthesis and paved the way to clinical application of deoxyribonucleic acid (DNA) array chips such as those sold under the name GENECHIP™. Kozal et al., Nature Medicine 2: 753-759 (1996). VLSIPS technology is disclosed in U.S. Pat. No. 5,143,854, PCT International patent applications WO 90/15070), WO 92/10092, and WO 95/11995; and Fodor et al., Science 251: 767-777 (1991).

Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls. Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Ausubel et al., Current Protocols in Molecular Biology (Greene Publishing and Wiley-Interscience, New York 1987). Useful hybridization conditions are also provided in, e.g., Tijessen, Hybridization With Nucleic Acid Probes, (Elsevier Science Publishers B.V., 1993) and Kricka, Nonisotopic DNA Probe Techniques, (Academic Press, San Diego, Calif., 1992).

When cDNA complementary to the RNA of a cell is made and hybridized to a microarray under suitable hybridization conditions, the level of hybridization to the site in the array corresponding to any particular gene will reflect the prevalence in the cell of RNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

U.S. Pat. No. 6,183,968 (to Bandman et al.) discloses polynucleotide probes that can be used as hybridizable array elements in a microarray, each of the polynucleotide probes having at least a portion of a gene which encodes a protein associated with cell proliferation.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., Genome Research 6:639-645 (1996)). Signals are recorded and, preferably, analyzed by computer, using commercially available methods. The abundance sort program of the invention described in U.S. Pat. No. 5,840,484 can be used to tabulate and sort by frequency the mRNA transcripts corresponding to each gene identified. Since some of the polynucleotide sequences are identified solely based on expression levels, it is not essential to know a priori the function of a particular gene in hemangioma derived stem cells.

Transcript image comparisons can be obtained by methods well known to those skilled in the art. Transcript levels and images can be obtained and compared, for example, by a differential gene expression assay based on a quantitative hybridization of arrayed DNA clones (Nguyen et al. Genomics 29:207-216 (1995), based on the serial analysis of gene expression (SAGE) technology (Velculescu et al. Science 270:484-487 (1995)), based on the polymerase chain reaction (Peng et al. Science 257:967-971 (1992), based on a differential amplification protocol (U.S. Pat. No. 5,545,522), or based on electronic analysis, such as comparative gene transcript analysis (U.S. Pat. No. 5,840,484) or the GEMTOOLS gene expression analysis program (Incyte Pharmaceuticals, Palo Alto, Calif., USA). Preferably, comparisons between two or more transcript profiles are performed electronically.

Measurement of the translational state may be performed according to several methods. For example, whole genome monitoring of protein (i.e., the "proteome,") can be carried out by constructing a microarray in which binding sites comprise immobilized, preferably monoclonal, antibodies specific to a plurality of protein species encoded by the cell genome.

The microarrays describe above can be employed in several applications including hemangioma diagnostics, prognostics and treatment regimens, drug discovery and development, toxicological and tumorgenicity studies, forensics, pharmacogenomics and the like.

In one embodiment, the microarray is used to monitor the progression of disease. Physicians can assess and catalog the differences in gene expression between healthy and hemangioma tissues by analyzing changes in patterns of gene expression compared with hemangioma derived stem cells from the patient. The stem cells of the present invention may also be used to monitor the efficacy of treatment. For some treatments with known side effects, the microarray is employed to "fine tune" the treatment regimen. A dosage is established that causes a change in genetic expression patterns indicative of successful treatment. Expression patterns associated with undesirable side effects are avoided. This approach may be more sensitive and rapid than waiting for the patient to show inadequate improvement, or to manifest side effects, before altering the course of treatment.

Alternatively, animal models which mimic infantile hemangioma, rather than patients, may be used to characterize expression profiles associated with a particular disease or condition. This gene expression data may be useful in diagnosing and monitoring the course of disease in a patient, in determining gene targets for intervention, and in testing novel treatment regimens.

Also, researchers can use the microarray to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to determine the molecular mode of action of a drug.

In various embodiments, the effects on the cell can be determined by measuring gene expression, protein abundances, protein activities, or a combination of such measurements. In various embodiments, modifications to a putative target in the cell can be made by modifications to the genes encoding the target, modification to abundances of RNAs encoding the target, modifications to abundances of target proteins, or modifications to activities of the target proteins. The present invention provides an improvement to these methods of drug discovery by providing the hemangioma derived stem cells, for a more precise drug discovery program.

An "expression profile" comprises measurement of a plurality of cellular constituents that indicate aspects of the biological state of a cell. Such measurements may include, e.g., RNA or protein abundances or activity levels. Aspects of the biological state of a cell of a subject, for example, the transcriptional state, the translational state, or the activity state, are measured. The collection of these measurements, optionally graphically represented, is called the "diagnostic profile." Aspects of the biological state of a cell which are similar to those measured in the diagnostic profile, e.g., the transcriptional state, are measured in an analogous subject or subjects in response to a known correlated disease state or, if therapeutic efficacy is being monitored, in response to a known, correlated effect of a therapy. The collection of these measurements, optionally graphically represented, is called herein the response profile." The response profiles are interpolated to predict response profiles for all levels of protein activity within the range of protein activity measured. In cases where therapeutic efficacy is to be monitored, the response profile may be correlated to a beneficial effect, an adverse effect, such as a toxic effect, or to both beneficial and adverse effects.

As is commonly appreciated, protein activities result from protein abundances; protein abundances result from translation of mRNA (balanced against protein degradation); and mRNA abundances result from transcription of DNA (balanced against mRNA degradation). Therefore, genetic level modifications to a cellular DNA constituent alters transcribed mRNA abundances, translated protein abundances, and ultimately protein activities. RNA level modifications similarly alter RNA abundance and protein abundances and activities. Protein level modifications alter protein abundances and activities. Finally, protein activity modifications are the most targeted modification methods. As is commonly appreciated, it is ultimately protein activities (and the activities of catalytically active RNAs) that cause cellular transformations and effects. Also, most drugs act by altering protein activities.

In one embodiment, cDNAs from two different cells (one being the hemangioma derived stem cells of the invention) are hybridized to the binding sites of the microarray. In the case of therapeutic efficacy (e.g., in response to drugs) one cell is exposed to a therapy and another cell of the same type is not exposed to the therapy. In the case of disease states one cell exhibits a particular level of disease state and another cell of the same type does not exhibit the disease state (or the level thereof). The cDNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular mRNA detected. The use of a two-color fluorescence labeling and detection scheme to define alterations in gene expression has been described, e.g., in Shena et al., Science 270:467-470 (1995). An advantage of using cDNA labeled with two different fluorophores is that a direct and internally controlled comparison of the mRNA levels corresponding to each arrayed gene in two cell states can be made, and variations due to minor differences in experimental conditions (e.g., hybridization conditions) will not affect subsequent analyses.

Gene expression profiles of purified stem cells could give clues for the molecular mechanisms of stem cell behavior. Terskikh A V et al., Proc Natl Acad Sci USA 98(14): 7934-7939 (2001) analyzed hematopoietic stem cells (HSC)-enriched cells by comparison with normal tissue and mouse neurospheres (a population greatly enriched for neural progenitor cells) by comparison with terminally differentiated neural cells, using cDNA microarray techniques and in situ hybridization, thus identifying potential regulatory gene candidates. The invention provides an improved method of drug discovery over the methods of Terskikh, in that the use of the hemangioma derived stem cells of the invention can provide a distinct set of drug targets when compared with a patient's normal tissue (such as from the area of the hemangioma) or compared with the other populations of cells obtained from the hemangioma.

Several other methods for utilizing DNA chips are known, including the methods described in U.S. Pat. Nos. 5,744,305; 5,733,729; 5,710,000; 5,631,734; 5,599,695; 5,593,839; 5,578,832; 5,556,752; 5,770,722; 5,770,456; 5,753,788; 5,688,648; 5,753,439; 5,744,306. U.S. Pat. No. 5,807,522 (to Brown et al.) discloses a method to monitor early changes in a cell that correlate with levels of a disease state or therapy and which precede detectable changes in actual protein function or activity.

Moreover, microarrays of genomic DNA from hemangioma derived stem cells can be probed for single nucleotide polymorphisms (SNP), to localize the sites of genetic mutations that cause cells to become tumorigenic. Guidance for such methods are available from commercial vendors and may be found in general genetic method books, such as those disclosed herein.

In some embodiments of the present invention, cells are analyzed by chromatin immunoprecipitation (ChIP). A complete protocol is provided by NimbleGen Systems Inc (Madison, Wis.). In brief, cells are grown, cross-linked with formaldehyde and sheared by sonication. In one aspect, anti-SALL4 antibody and rabbit serum are used for ChIP. ChIP-purified DNA is blunt-ended, ligated to linkers and subjected to low-cycle PCR amplification. Promoter tiling arrays may be obtained from NimbleGen. The promoter array may be designed as a single array containing 2.7 kb of each promoter region. The promoter region is covered by 50-75 mer probes at roughly 100 bp spacing dependent on the sequence composition of the region. The arrays are hybridized, and the data may be extracted according to NimbleGen standard procedures. Confirmation of the predicted binding sites is performed using Quantitative real-time PCR analysis of the amplicons that are applied to the arrays.

A custom microarray may be obtained commercially (e.g., from NimbleGgen Madison, Wis.) using maskless array synthesis. Each gene is compared with all others using the BLAST program to remove redundancies. Ten probe pairs for each target are selected from the 3' 1 kb of each target. Probes are spaced evenly over the length of the target region (<1 kb), so that the exact spacing depended on the length of the target sequence. Each probe may be about 10, about 20, or about 25 nucleotides in length. In one aspect, the probes are 24 nucleotides in length. For each perfect match probe there is also a mismatch probe, which differs by one or more nucleotides.

Labeled cDNA is hybridized to the oligonucleotide probes on the microarray. After washing, arrays are stained with an affinity tag (e.g., streptavidin-Cy3 conjugate, Amersham Biosciences, Piscataway, N.J.), followed by washing and a blow dry step. Slides may be scanned using a GenePix 4000B microarray scanner (Axon Instruments, Union City, Calif., USA), and the feature intensities extracted from the TIF files are calculated by the scanner software using a proprietary application developed at NimbleGen (Madison, Wis., USA). This application calculates mean signal intensities for the pixels that define each feature (3×3 grid of pixels). The intensities for each gene are calculated by taking the mean of the intensities for the perfect match probes specific to each target minus the mean of the intensity of the mismatch probes. Probes that differ from the mean for the set by more than 3 SD are removed from the set and the mean recalculated. Average differences (recalculated mean) are used for subsequent analysis.

The hemangioma derived stem cells of the invention can be used to raise anti-stem cell antibodies. In one embodiment, the method involves obtaining an enriched population of hemangioma derived stem cells or isolated hemangioma derived stem cells; treating the population to prevent cell replication (for example, by irradiation); and administering the treated cell to a human or animal subject in an amount effective for inducing an immune response to the stem cells. For guidance as to an effective dose of cells to be injected or orally administered; see, U.S. Pat. Nos. 6,218,166, 6,207,147, and 6,156,305. In another embodiment, the method involves obtaining an enriched population of hemangioma derived stem cells or isolated hemangioma derived stem cells; mixing the stem cells in an in vitro culture with immune effector cells (according to immunological methods known in the art) from a human subject or host animal in which the antibody is to be raised; removing the immune effector cells from the culture; and transplanting the immune effector cells into a host animal in a dose that is effective to stimulate an immune response in the animal.

The stem cells of the present invention may also be used to prepare monoclonal antibodies. Monoclonal antibodies to hemangioma derived stem cells may be prepared using any technique which provides for the production of antibody molecules by continuous cell lines in culture. These include, but are not limited to, the hybridoma technique, the human B-cell hybridoma technique, and the EBV-hybridoma technique (see, e.g., Kozbor, D. et al., J. Immunol. Methods 81:31-42 (1985); Cote R J et al. Proc. Natl. Acad. Sci. 80:2026-2030 (1983); and Cole S P et al. Mol. Cell. Biol. 62:109-120 (1984)).

In addition, techniques developed for the production of "chimeric antibodies," such as the splicing of mouse antibody genes to human antibody genes to obtain a molecule with appropriate antigen specificity and biological activity, may be used (see, e.g., Morrison S L et al. Proc. Natl. Acad. Sci. 81:6851-6855 (1984); Neuberger M S et al. Nature 312:604-608 (1984); and Takeda S et al. Nature 314:452-454 (1985)).

Various immunoassays may be used for screening to identify antibodies having the desired specificity. Numerous protocols for competitive binding or immunoradiometric assays using either polyclonal or monoclonal antibodies with established specificities are well known in the art.

The antibody can also be a humanized antibody. The term "humanized antibody," as used herein, refers to antibody molecules in which the amino acid sequence in the non-antigen binding regions has been altered so that the antibody more closely resembles a human antibody, and still retains its original binding ability. Antibodies are humanized so that they are less immunogenic and therefore persist longer when administered therapeutically to a patient.

Human antibodies can be generated using the XENOMOUSE™ technology from Abgenix (Fremont, Calif., USA), which enables the generation and selection of high affinity, fully human antibody product candidates to essentially any disease target appropriate for antibody therapy. See, U.S. Pat. Nos. 6,235,883, 6,207,418, 6,162,963, 6,150,584, 6,130,364, 6,114,598, 6,091,001, 6,075,181, 5,998,209, 5,985,615, 5,939,598, and 5,916,771; Yang X et al., Crit. Rev Oncol Hemato 38(1): 17-23 (2001); Chadd H E & Chamow S M. Curr Opin Biotechnol 12(2):188-94 (2001); Green L L, Journal of Immunological Methods 231 11-23 (1999); Yang X-D et al., Cancer Research 59(6): 1236-1243 (1999); and Jakobovits A, Advanced Drug Delivery Reviews 31: 33-42 (1998). Antibodies with fully human protein sequences are generated using genetically engineered strains of mice in which mouse antibody gene expression is suppressed and functionally replaced with human antibody gene expression, while leaving intact the rest of the mouse immune system.

Moreover, the generation of antibodies directed against markers present in or on hemangioma derived stem cells of the present invention may be used as a method of identifying targets for drug development. The antibodies that are raised in an immune response to the stem cells of the present invention may be used to identify antigenic proteins on the hemangioma derived stem cells using methods known in the art (Harlow, Using Antibodies: A Laboratory Manual (Cold Spring Harbor Press, Cold Spring Harbor, N.Y., 1999)) and can further be used to identify polynucleotides coding for such proteins (Sambrook et al., Molecular Cloning: A Laboratory Manual (Cold Spring Harbor Press, Cold Spring Harbor, N.Y., 1989); Current Protocols in Molecular Biology, Ausubel et al., eds., (Wiley Interscience, New York, 1993)). Once identified, the proteins and polynucleotides can be compared with other proteins and polynucleotides previously identified to be involved in infantile hemangioma. In one embodiment, the XENOMOUSE™ technology to produce fully human antibodies can be used to generate antibodies directed against drug development targets (see, Jeffrey Krasner, Boston Globe (Jul. 25, 2001) at F4). The present invention provides an improvement to these antibody-based methods of drug discovery by providing the hemangioma derived stem cells, to which the immune response is raised, for a more precise drug discovery program.

Alternatively, methods for raising an immune response can take advantage of the "stem cell" qualities of the hemangioma derived stem cell of the invention. Hemangioma derived stem cells, hemangioma derived stem cell protein extracts, purified proteins from hemangioma derived stem cells, or proteins derived from the expression of cDNAs from hemangioma derived stem cells (see, above for genetic modification of hemangioma derived stem cells) to induce an immune response in an animal. The immune response can be directed against hemangioma cells, as shown by standard immunological methods. For example, the hemangioma derived stem cells (enriched populations of isolated cells) or proteins can be contacted with dendritic cells in culture, antigen presenting cells in culture, or antigen presenting cells and T cells in culture. Then antigen-stimulated cells are infused back into the subject.

Alternatively, the hemangioma derived stem cells of the invention can be genetically engineered to promote an immune response against the stem cells. For example, hematopoietic stem cells can be engineered to contain a T-cell receptor targeting a tumor stem cell antigen. See, U.S. Pat. Nos. 5,914,108 and 5,928,638. Thus, T cell receptors that recognize antigens expressed by tumor stem cells can be identified, then cloned into hematopoietic stem cells. The engineered hematopoietic stem cells may then be transplanted into a subject and allowed to engraft, giving rise to large numbers of T cells that express receptors recognizing the tumor stem cells. In a similar fashion, by increasing the numbers of hemangioma derived stem cell-specific T cells, an anti-hemangioma immune response may be potentiated.

Other means are also available for increasing the anti-hemangioma immune response, including using the hemangioma derived stem cells as the basis of a vaccine, using the hemangioma derived stem cells to stimulate antigen presenting dendritic cells, and using the hemangioma derived stem cells as an innoculum to generate anti-hemangioma derived stem cell antibodies. Hemangioma derived stem cells may be used as a vaccine by killing a subject's hemangioma derived stem cells, such as by irradiation, and re-administering the killed stem cells back into the subject in a physiological/pharmaceutically and immunologically acceptable carrier, for the purpose of generating an immune response against the hemangioma derived stem cells. See, U.S. Pat. No. 4,960,716, in which antibodies were raised to membrane vesicle preparations of breast carcinoma cell cells; U.S. Pat. No. 4,584,268, in which anti-human mammary epithelial antibody was produced from a membrane fraction of delipidated human milk fat globules.

Dendritic cells from a subject may be cultured in vitro and killed hemangioma derived stem cells from the same subject may be added to the cultures to stimulate the dendritic cells. The activated dendritic cells, presenting hemangioma derived stem cell antigens, may then be re-administered to the subject to stimulate the subject's anti-hemangioma response. Finally, hemangioma derived stem cells can be administered to an animal such as a mouse, rat, hamster, goat, sheep, rabbit, or donkey to generate antibodies against the stem cells. Preferably, monoclonal anti-hemangioma derived stem cell antibodies are made in mouse, rat, or hamster. Monoclonal antibodies that are made in this way can then be administered to subjects, or first humanized (as described above) and then administered to subjects, to promote an immune response against the hemangioma derived stem cells in the subject.

Furthermore, adenoviral vectors have proven especially useful for gene transfer into eukaryotic cells for vaccine development. Graham F L & Prevec L, In Vaccines: New Approaches to Immunological Problems, Ellis R V ed., 363-390 (Butterworth-Heinemann, Boston, 1992).

The identification of biological pathways is an important part of modem drug discovery process. Biological pathways in hemangioma derived stem cells and other cell populations obtained from hemangiomas, particularly pathways involved in drug actions, i.e., pathways that originate at a drug target (e.g., proteins), can be identified for use as shown by U.S. Pat. No. 5,965,352.

In one set of methods, drugs are screened to determine the binding of test compounds to receptors, in which the binding activates a cell's biological pathway to cause expression of reporter polypeptides. Frequently the reporter polypeptides are coded for on recombinant polypeptides, in which the coding polynucleotide is in operable linkage with a promoter.

The terms "operably associated" or "operably linked," as used herein, refer to functionally related polynucleotides. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The detectable signal can be fluorescence, absorbence, or luminescence, depending on the reporter polypeptide, which can be, for example, luciferase (firefly luciferase, Vibrio fisceri luciferase, or Xenorhabdus luminescens luciferase), green fluorescent protein, green fluorescent protein variant, chloramphenicol acetyltransferase, $\beta$-glucuronidase, $\beta$-galactosidase, neomycin phosphotransferase, guanine xanthine phosphoribosyltransferase, thymidine kinase, $\beta$-lactamase, alkaline phosphatase, invertase, amylase (for yeast based assays) human growth hormone (for activity based assays). The fluorescent detectable signal can be fluorescence resonance energy transfer (FRET), bioluminescence resonance energy transfer (BRET), time-resolved fluorescence (TRF) or fluorescence polarization (FP). Where appropriate, the detectable signal is detected by a machine such as a fluorometer, luminometer, fluorescence microplate reader, dual-monochromator microplate spectrofluorometer, spectrophotometer, confocal microscope (laser scanner), or a charge-coupled device (CCD). The detectable signal is determined by comparing the amount of signal produced when the reporter polypeptide is expressed in the hemangioma derived stem cell with the signal produced when the reporter polypeptide is not expressed in the hemangioma derived stem cell.

Another technique for drug screening provides for high throughput screening of compounds (see, e.g., PCT application WO 84/03564.) In this method, large numbers of different small test compounds are synthesized on a solid substrate, such as plastic pins or some other surface. The test compounds are reacted with hemangioma derived stem cells, or portions thereof, and washed. Bound hemangioma stem cells are then detected by methods well known in the art, using commercially available machinery and methods, for example, the Automated Assay Optimization (AAO) software platforms (Beckman, USA) that interface with liquid handlers to enable direct statistical analysis that optimizes the assays; modular systems from CRS Robotics Corp. (Burlington, Ontario), liquid handling systems, readers, and incubators, from various companies using POLARA™ (CRS), an open architecture laboratory automation software for a Ultra High Throughput Screening System; 3P (Plug&Play Peripherals) technology, which is designed to allow the user to reconfigure the automation platform by plugging in new instruments (ROBOCON, Vienna, Austria); the ALLEGRO™ system or STACCATO™ workstation (Zymark), which enables a wide range of discovery applications, including HTS, ultra HTS, and high-speed plate preparation; MICROLAB Vector software (Hamilton Co., Reno, Nev., USA) for laboratory automation programming and integration; and others.

For any of these machines and methods, the assays measure a response the target cells (hemangioma derived stem cells or genetically modified hemangioma derived stem cells) that provides detectable evidence that the test compound may be efficacious. The detectable signal is compared to control cells and the detectable signal identified by subtraction analysis. The relative abundance of the differences between the "targeted" and "untargeted" aliquots are simultaneously compared using a "subtraction" analysis (differential analysis) technique such as differential display, representational difference analysis (RDA), GEM-Gene Expression Microarrays (U.S. Pat. No. 5,545,531), suppressive subtraction hybridization (SSH) and direct sequencing (PCT patent application WO 96/17957). The subtraction analysis can include the methods of differential display, representational differential analysis (RDA), suppressive subtraction hybridization (SSH), serial analysis of gene expression (SAGE), gene expression microarray (GEM), nucleic acid chip technology, or direct sequencing.

Hemangioma derived stem cells of the present invention are particularly useful in the drug development process because hemangioma stem cells provide a limited and enriched set of targets for drug development. One of the most important steps in rational drug design is the identification of a target, the molecule with which the drug itself interacts.

Likewise, the genetically modified hemangioma derived stem cell of the present invention is particularly useful in the drug development. For example, the genetically modified stem cell can contain polynucleotide with a promoter operably linked to the polynucleotide encoding a reporter polypeptide. The reporter polypeptide is expressed in the stem cell after a receptor of the stem cell is activated by binding to a test compound or inactivated by binding to a test compound. Such a detectable signal makes the genetically modified hemangioma derived stem cell appropriate for use in high throughput screening (HTS).

The detectable signal can be a result of a positive selection or a negative selection. The positive selection includes manipulations that test the ability of cells to survive under specific culture conditions, ability to express a specific factor, changes in cell structure, or differential gene expression.

The invention also provides a kit comprising packaging material and a primary reagent contained within said packaging material. The primary reagent is a hemangioma stem cell preparation as described above. The packaging material includes a label that indicates that the primary reagent can be used for identifying an agent for reducing hemangiomas. Also, the invention provides a kit for determining the activity level of a particular polynucleotide or protein in a cell. Such kits contain arrays or microarrays containing a solid phase, e.g., a surface, to which are bound, either directly or indirectly, hemangioma derived stem cells (enriched populations of or isolated), polynucleotides extracted from such hemangioma derived stem cells, or proteins extracted from such hemangioma derived stem cells. The kit may also contain probes that are hybridized or bound to the hemangioma derived stem cell components at a known location of the solid phase. These probes consist of nucleic acids of known, different sequence, with each nucleic acid being capable of hybridizing to an RNA species or to a cDNA species derived therefrom. In particular, the probes contained in the kits of this invention are nucleic acids capable of hybridizing specifically to nucleic acid sequences derived from RNA species which are known to increase or decrease in response to perturbations correlated to the particular diseases or therapies to be monitored by the kit. The probes contained in the kits of this invention preferably substantially exclude nucleic acids which hybridize to RNA species that are not increased or decreased in response to perturbations correlated to the particular levels of disease states or therapeutic effects to be determined by the kit.

The following examples are intended to illustrate but not limit the invention.

EXAMPLES

Example 1

Isolation of Tumor Spheres

Tissue samples were isolated from superficial raised patches on the skin of male and female infants (less than 1 year), prior to involution. Upon receipt, the tissue was minced and digested with collagenase for 2 hours at 37° C. Following digestion and several wash steps, the tissue mixture was then filtered through a 100 µm cell strainer and grown in culture using KNOCKOUT™ Dulbecco's Modified Eagle's Medium (DMEM), 10% KNOCKOUT™ Serum, 1× non-essential amino acids (NEAA), and 20 µg/ml basic-fibroblast growth factor (bFGF). Following growth of this primary culture for approximately three days, tumor spheres will spontaneously form from the homogenous mixture of primary culture. These spheres are collected using collagenase digestion, washed, and plated at a density of 200 cells per milliliter with DMEM-F12 nutrient mix, 20 µg/ml bFGF and NEAA on low-attachment plates. The tumor spheres form and propagate using collagenase digestion, which digest the spheres to single cells. These single cells then form additional tumor spheres in vitro.

Figure 2:
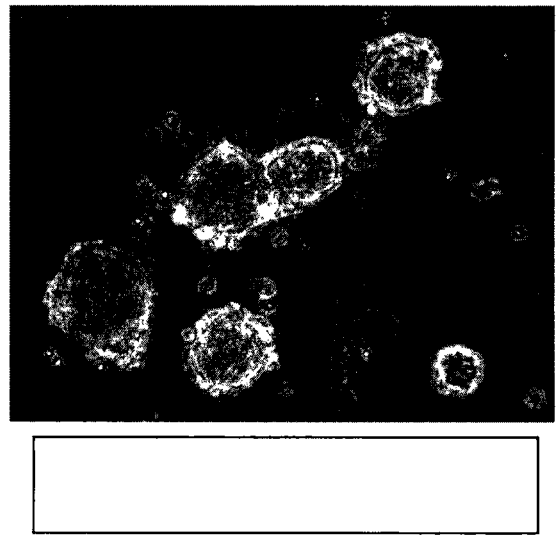
FIG. 2 is a photomicrograph showing the intermediate formation of tumor spheres in culture.
Figure 3:
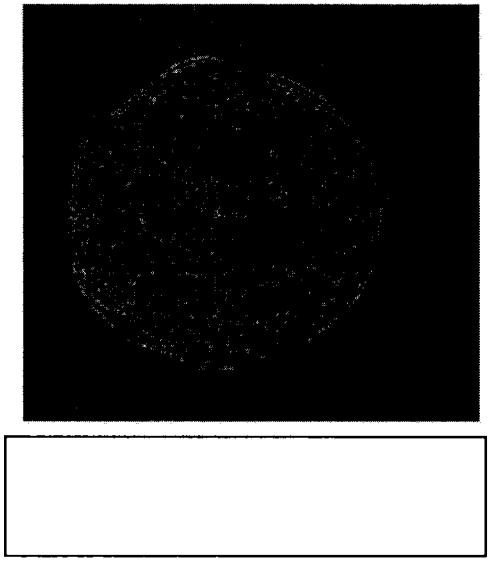
FIG. 3 is a photomicrograph of a tumor sphere derived from human hemangioma tissue under high power magnification.
Figure 4:
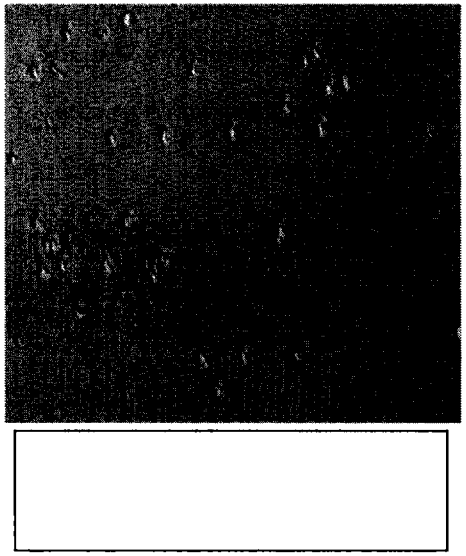
FIG. 4 is a photomicrograph showing tumor spheres dissociated into single cells.
Figure 5:
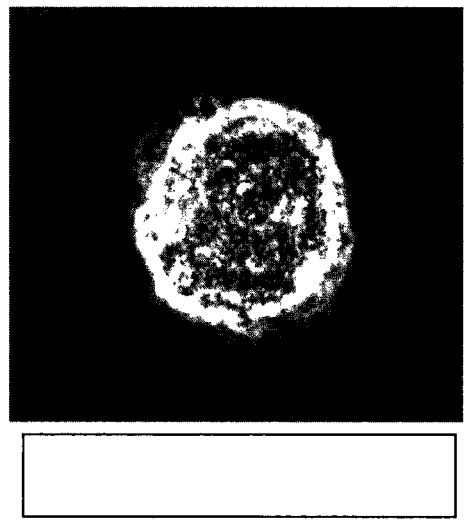
FIG. 5 is a photomicrograph showing the tumor sphere formed from a single cell colony.

The tumor spheres derived from fresh human hemangioma tissues grow for an indefinite period of time under serum-free conditions (FIGS. 1-3). These tumor spheres bear similar key properties of all normal stem cells and tumor stem cells, that is, their unique ability to self-renew. One method to determine whether tumor sphere cells have self-renewal capacity is to test their capability for serial passages. The tumor spheres dissociated into single cell suspensions continued to grow single cells in culture for a week (FIG. 4). The single cell suspension was able to expand and form new tumor spheres within one to two weeks (FIG. 5).

Figure 6:
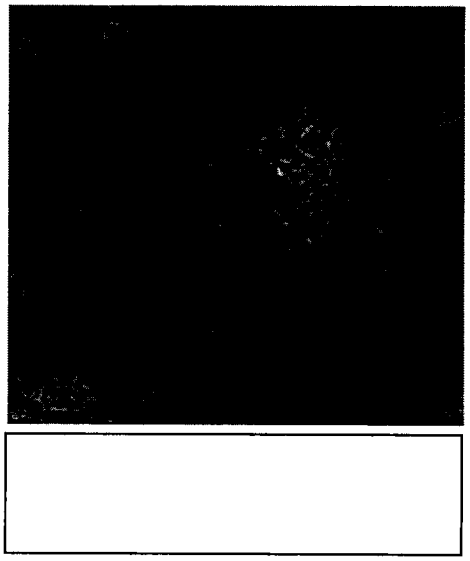
FIG. 6 is a photomicrograph showing endothelial-like cells differentiated from a single cell.

Another key property of stem cells is their ability to differentiate into mature cells. To assess whether hemangioma tumor sphere cells are able to differentiate into mature cells, tumor cells were cultured in appropriate growth factors. Hemangioma tumor spheres grown in DMEM/F12+50 µg/ml VEGF+NEAA for 72 hours differentiated into the endothelial-like tissue. Phase-contrast microscopy analysis revealed changes in the cell morphology within 24 hours and endothelial-like tissues were formed (FIG. 6).

Figure 8:
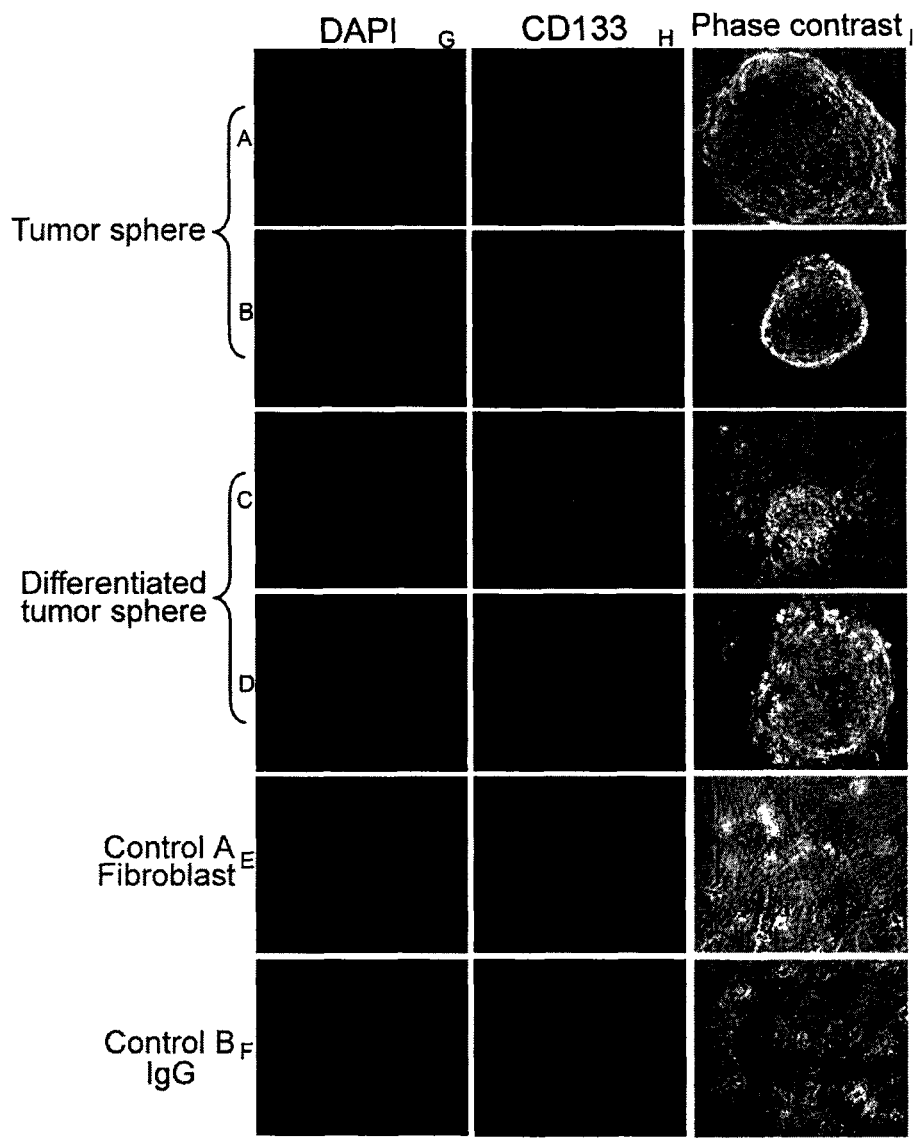
FIG. 8 shows immunofluorescent staining of CD133-positive and CD133-low hemangioma tumor spheres following induced differentiation. A and B are infantile hemangioma tumor spheres showing high expression of the progenitor cells in various organ systems. C and D are tumor spheres differentiating toward the endothelial lineage following treatment with VEGF. E shows fibroblast cells derived form the same primary culture as the hemangioma tumor spheres do not express CD133. F is a negative control antibody demonstrating the specificity of immunostaining.

Although tumor sphere capacity for self renewal and differentiation were demonstrated, demonstration of lineage commitment to endothelial lineage by the tumor spheres was sought. Immunohistochemical staining of the hemangioma tumor spheres revealed that the cells were negative for CD34, and endothelial marker. In contrast, these cells highly expressed the SALL4 protein, a marker for pluripotency expressed in embryonic stem cells and cancer cells (FIG. 8).

Figure 7:
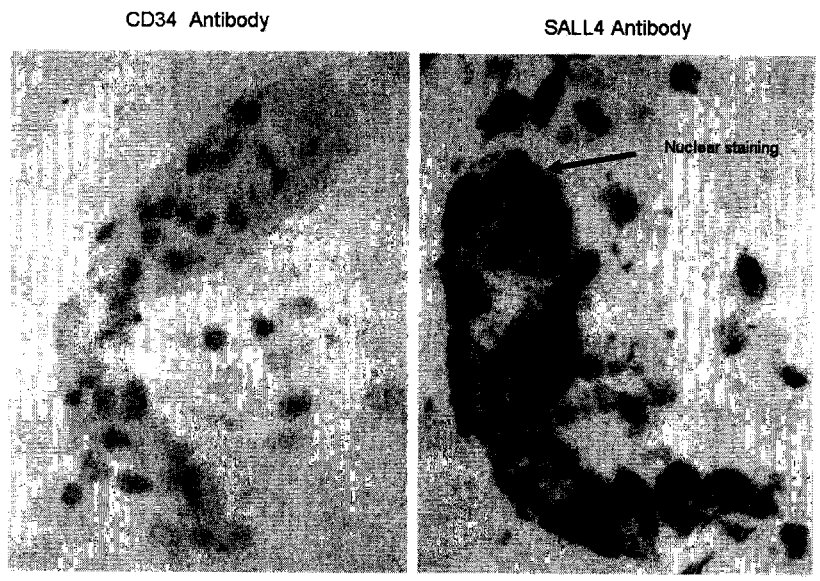
FIG. 7 shows immunohistochemical staining of tumor sphere tissues with CD34, a marker for differentiated endothelial cells and SALL4, a pluripotency marker associated with ES cells and cancer stem cells.

To further demonstrate that the infantile hemangioma tumor spheres are pluripotent, immunofluorescent staining was used to demonstrate the expression of glycoprotein CD133. CD133 is a cell surface protein expressed in hematopoietic stem cells, neuronal stem cells, glial stem cells, and importantly, endothelial progenitor cells. Expression of this protein serves as a marker for primitive cells. As shown in FIG. 7, tumor spheres were immuno-positive for the stem cell marker CD133 (FIGS. 8A and 8B), while fibroblasts generated from the same primary tissues sample were CD133 negative (FIG. 8E). After adding VEGF to the culture medium, partially differentiated tumor spheres were only GFP positive in undifferentiated cells with GFP-negative fibroblasts surrounding the spheres. Expression of CD133 in the hemangioma tumor spheres is consistent with their endothelial lineage.

Taken together, these data suggest that tumor spheres have the stem cell properties of self-renewal and differentiation. Tumor stem cells have been known to resist to chemotherapy and are likely responsible for the initiation and progression of disease by maintaining the production of new tumor cells. Therefore, the tumor spheres derived from fresh infantile hemangioma tissues have many potential uses.

Example 2

ChIP Assay

Isolated cells from tumor spheres ($1\times10^6$ cells/well in 6-well plates), are processed using a ChIP Assay Kit (Upstate, Charlottesville, Va.) following the manufacture's protocol. Briefly, cells are cross-linked by adding formaldehyde (27 µl of 37% formaldehyde/ml) and incubated for 10 min. Then, chromatin is sonicated to an average size of approximately 500 bp and immunoprecipitated with SALL4 antibodies, pre-immune serum, or anti-HA (hemagglutination) antibody. Antibodies for histone modifications, histone H3 trimethy K4 and histone H3 dimethy K79, may be purchased from Abeam (Cambridge, Mass.). Histone-DNA crosslinks are reversed by heating at 65° C. followed by digestion with proteinase K (Invitrogen, Carlsbad, Calif.). DNA is recovered by using a PCR purification kit (Qiagen, Valencia, Calif.) and then used for PCR or QRT-PCR (quantitative real time polymerase chain reaction).

Although the invention has been described with reference to the above examples, it will be understood that modifications and variations are encompassed within the spirit and scope of the invention. Accordingly, the invention is limited only by the following claims.

We claim herein:

1. A method of isolating stem cells comprising:
   a) isolating cells from hemangioma tissue;
   b) culturing the cells of step (a) in serum free media and fibroblast growth factor in a low attachment plate until tumor spheres are formed;
   c) isolating cells from the tumor spheres; and
   d) culturing the isolated cells of step (c) in serum free media, wherein the isolated stem cells are capable of differentiating into endothelial-like tissue when contacted with VEGF.

2. The method of claim 1, wherein the stem cell expresses SALL4.

* * * * *